(12) United States Patent
Gastaldo et al.

(10) Patent No.: US 9,389,189 B2
(45) Date of Patent: Jul. 12, 2016

(54) DARK-FIELD SEMICONDUCTOR WAFER INSPECTION DEVICE

(71) Applicant: Altatech Semiconductor, Montbonnot-Saint-Martin (FR)

(72) Inventors: Philippe Gastaldo, Pontcharra (FR); Frederic Pernot, Saint-Egreve (FR)

(73) Assignee: Altatech Semiconductor, Montbonnot-Saint-Martin (FR)

( * ) Notice: Subject to any disclaimer, the term of this patent is extended or adjusted under 35 U.S.C. 154(b) by 0 days.

(21) Appl. No.: 14/350,978

(22) PCT Filed: Oct. 9, 2012

(86) PCT No.: PCT/FR2012/000405
§ 371 (c)(1),
(2) Date: Apr. 10, 2014

(87) PCT Pub. No.: WO2013/060945
PCT Pub. Date: May 2, 2013

(65) Prior Publication Data
US 2014/0268121 A1    Sep. 18, 2014

(30) Foreign Application Priority Data
Oct. 10, 2011  (FR) ..................................... 11 03078

(51) Int. Cl.
*G01N 21/95*    (2006.01)
*G01N 21/94*    (2006.01)

(52) U.S. Cl.
CPC ............ *G01N 21/9501* (2013.01); *G01N 21/94* (2013.01)

(58) Field of Classification Search
CPC ........................... G01N 21/9501; G01N 21/94
See application file for complete search history.

(56) References Cited

U.S. PATENT DOCUMENTS

| | | | | |
|---|---|---|---|---|
| 3,639,066 A | * | 2/1972 | Kantorski et al. | .......... 356/239.2 |
| 4,423,331 A | * | 12/1983 | Koizumi | ................ G01N 21/88 |
| | | | | 250/559.16 |
| 4,597,665 A | * | 7/1986 | Galbraith et al. | .......... 356/239.8 |
| 4,630,276 A | | 12/1986 | Moran et al. | |
| 4,740,708 A | | 4/1988 | Batchelder | |

(Continued)

FOREIGN PATENT DOCUMENTS

| | | |
|---|---|---|
| EP | 1553406 A1 | 7/2005 |
| WO | 2007084124 A1 | 7/2007 |

OTHER PUBLICATIONS

French Search Report for French Application No. 1103078 dated May 18, 2012, 2 pages.

(Continued)

*Primary Examiner* — Michael A Lyons
*Assistant Examiner* — Dominic J Bologna
(74) *Attorney, Agent, or Firm* — TraskBritt (57) ABSTRACT

The invention relates to a dark-field semiconductor wafer inspection device including, in the following order, a light source for emitting an incident beam to a wafer along a first axis, a concentrator that is symmetrical in relation to a plane passing through the first and second axes and is provided with a mirror that is elliptically cut along a plane perpendicular to an axis perpendicular to the first axis and has a generator parallel to the first axis, parallel first and second slits being set up sideways in first and second portions of the concentrator at the points for concentrating the light that is scattered by the wafer and reflected by the second and first portions of the concentrator, respectively, and a photomultiplier using a slit.

12 Claims, 11 Drawing Sheets

(56) References Cited

U.S. PATENT DOCUMENTS

| | | | | |
|---|---|---|---|---|
| 4,965,454 | A | * | 10/1990 | Yamauchi .............. G01N 21/94 250/228 |
| 5,058,982 | A | * | 10/1991 | Katzir ................ G01N 21/8806 385/15 |
| 5,076,692 | A | * | 12/1991 | Neukermans .......... G01N 21/94 250/574 |
| 6,130,749 | A | * | 10/2000 | Meeks et al. .................. 356/630 |
| 2003/0169916 | A1 | | 9/2003 | Hayashi et al. |
| 2004/0169850 | A1 | * | 9/2004 | Meeks ....................... 356/237.2 |
| 2008/0285022 | A1 | * | 11/2008 | Tsuji .......................... 356/237.4 |

OTHER PUBLICATIONS

International Preliminary Report on Patentability for International Application No. PCT/FR2012/000405 dated Apr. 15, 2014, 8 pages.
International Search Report for International Application No. PCT/FR2012/000405 dated Feb. 18, 2013, (translation included) 7 pages.
International Written Opinion for International Application No. PCT/FR2012/000405 dated Feb. 18, 2013, (translation included) 13 pages.

* cited by examiner

DARK-FIELD SEMICONDUCTOR WAFER INSPECTION DEVICE

CROSS-REFERENCE TO RELATED APPLICATIONS

This application is a national phase entry under 35 U.S.C. §371 of International Patent Application PCT/FR2012/000405, filed Oct. 9, 2012, designating the United States of America and published as International Patent Publication WO 2013/060945 A1 on May 2, 2013, which claims the benefit under Article 8 of the Patent Cooperation Treaty and under 35 U.S.C. §119(e) to French Patent Application Serial No. 11/03078, filed Oct. 10, 2011, the disclosure of each of which is hereby incorporated herein in its entirety by this reference.

TECHNICAL FIELD

The invention relates to the field of semiconductor wafer inspection and of inspection machines.

The invention is more particularly focused on inspection with the purpose of detecting defects, notably contamination by particles, or scratches. The defects may have an impact on the manufacture of micro-electronic products or relating to nanotechnologies by making some products non-functional.

BACKGROUND

A so-called "dark field" inspection was proposed in U.S. Pat. Nos. 4,630,276 and 4,740,708. The inspection is said to be a dark-field inspection since an absence of a defect is expressed by a dark image. In the absence of any defect, the incident beam is reflected. Emphasis is laid on the light scattered by the inspected surface of the semiconductor wafer. In the case when a defect is present, a portion of the incident beam is scattered. The scattered photons are then captured in order to infer therefrom information relating to the defects.

The applicants have identified a need for a compact inspection machine with high accuracy, not very sensitive to the direction of the defects, having a low manufacturing cost and a short inspection time.

The invention will improve the situation.

BRIEF SUMMARY

The device for inspecting semiconductor wafers comprises a light source emitting an incident beam toward a wafer along a first axis, a concentrator provided with a mirror that is symmetrical relative to a plane passing through the first and second axes, having an elliptical cross-section in a plane perpendicular to a second axis, the second axis being perpendicular to the first axis, and having a generatrix parallel to the first axis, first and second parallel slits laterally made in the first and second portions of the concentrator at the points of concentration of the light scattered by the wafer and reflected by the first and second portions of the concentrator, respectively, a member for collecting the light, positioned in each slit, and a member for measuring the light intensity of the collected light, in this order. It is thus possible to collect a very large portion of the light scattered by the surface of the semiconductor wafer and to send it toward the parallel slits, and this for an inspected face.

In an embodiment, the incident beam passes between the first and second portions of the concentrator. The reflected beam may pass between the first and second portions of the concentrator.

In an embodiment, the length of the concentrator along the second axis is greater than the diameter of the wafer. The rate for collecting the scattered light is thereby optimized.

In an embodiment, a slit is made at the top of the concentrator in order to let through the incident beam, the slit being elongated along the second axis.

In an embodiment, the device comprises a member for holding the wafer by the edges of the wafer, comprising supporting fingers, and at least one holding jaw.

In an embodiment, each portion of the concentrator has a focus, from among the two foci of the ellipse, substantially positioned in the slit of the other portion. The other focus is substantially positioned at the point where the incident beam encounters the surface of the wafer. Thus both portions have a common focus in this encounter point. The light beam scattered by the wafer and reflected by each portion of the concentrator is concentrated in the slit of the other portion. A focus of a portion of the concentrator is positioned at the location of the slit of the other portion. The light-collecting member comprises a web of optical fibers provided with two ends, one end of which is positioned on one of the foci of the opposite elliptical reflector. The second end of the web of optical fibers may result in a light sensor transforming the latter into an electric signal.

In an embodiment, the first axis is normal to the wafer. The reflected beam passes through the same path as the incident beam.

In an embodiment, the device comprises a mechanism for translating the wafer relative to the incident beam, parallel to a third axis perpendicular to the first and second axes. The device may comprise a specific scanning mechanism for displacing the incident beam translationally along the second axis. It is thus possible to inspect the surface of the wafer by scanning it.

In an embodiment, the device comprises a mechanism for rotating the wafer relative to the incident beam, along an axis parallel to the first axis. The rotation mechanism comprises a multi-arm support configured for supporting a plate and pivoting it in a selected angle. It is possible to pivot the wafer by an angle of 90° between two inspection steps in order to carry out a cross-inspection providing omnidirectional detection of the defects of a wafer surface.

In an embodiment, the elliptical mirror is defined by two distinct ellipses having a common focus. The common focus is positioned at the intersection location of the incident beam and of the inspected surface of the substrate. The other focus of each ellipse is positioned on the slit made in the other ellipse defining the other mirror portion, a slit where the light-collecting member is found, for example, an end of a web of optical fibers.

In an embodiment, the light source comprises, in this order, a laser emitter for emitting an incident beam, an optical isolator, a beam extender, also called an expander, a rotary polygonal mirror and a F-Theta lens positioned downstream from the rotary polygonal mirror in order to linearize the displacement of the beam relative to the focal plane. The rotation of the polygonal mirror allows a scan of the incident beam perpendicularly to the direction of translational displacement of the wafer. The device may comprise a first deflecting mirror positioned between the optical isolator and the beam extender and a second deflecting mirror positioned between the F-Theta lens and the wafer.

Advantageously, a set of two devices as described above is provided. The devices are positioned facing each other in order to inspect both faces of a same wafer, simultaneously. The inspection is preferably carried out with different wavelengths of incident beams.

In an embodiment, a device for inspecting semiconductor wafers comprises a light source for emitting an incident beam toward a wafer, a member for shaping the light scattered by the wafer, a member for processing the shaped light and a mechanism for rotating the wafer, comprising a multi-arm support configured for supporting the wafer and pivoting it by a selected angle. The incident beam is located in a substantially planar cover.

In an embodiment, the arms of the support are positioned in a star configuration.

In an embodiment, the rotating mechanism is positioned at a distance from the path of the incident beam.

In an embodiment, the multi-arm support is configured for pivoting the wafer by an angle of 90°.

In an embodiment, the device for inspecting semiconductor wafers comprises two symmetrical portions for simultaneously inspecting the opposite faces of a wafer. Each portion comprises a light source emitting an incident beam toward the wafer, a member for shaping the light scattered by the wafer, a filter receiving a shaped light, a member for processing the filtered light, the light sources of each portion being monochromatic with wavelengths shifted by at least 2%.

Advantageously, the shift in wavelengths is greater than 10 nm.

In an embodiment, the device for inspecting the semiconductor wafer comprises a laser source for emitting an incident beam, a beam extender, a rotary polygonal mirror and an F-Theta lens positioned downstream from the rotary polygonal mirror in order to linearize the displacement of the beam relative to the focal plane. In order to reduce the dimension of the whole, a rectangular deflecting mirror may be positioned between the F-Theta lens and the wafer. A deflecting mirror may be positioned upstream between the optical isolator and the beam extender.

In an embodiment, the device comprises a member for collecting the light scattered by the wafer and a member for processing the collected light.

Thus, the incident beam performs a scan over the width of the wafer while maintaining normal or quasi-normal incidence to the surface while the wafer moves in translation. In order to maintain the incident beam normal or quasi-normal, the incident beam is sent back by a rectangular deflecting mirror from the exit of the F-Theta lens toward the wafer.

A method for inspecting semiconductor wafers comprises:
emission of an incident beam toward a wafer, along a first axis, by an emitting light source,
concentration of the light scattered by the surface of the wafer toward the first and second parallel slits by the first and second portions of a concentrator provided with a mirror that is relative to a plane passing through the first and second axes, having an elliptical cross-section along a plane perpendicular to a second axis, the second axis being perpendicular to the first axis, and having a generatrix parallel to the first axis, the first and second slits being laterally made in the first and second portions at the concentration points of the light scattered by the wafer and reflected by the second and first portions of the concentrator, respectively,
collecting the light in each slit, and
measuring the light intensity of the collected light.

The incident beam and the reflected beam may pass between the first and second portions of the concentrator. The wafer may be rotated by 90° around an axis parallel to the first axis between a first inspection step and a second inspection step. The rotation may be performed between two translation steps allowing the wafer to be moved away from the concentrator. This translation may be performed in a plane perpendicular to the first axis. During an inspection step, the wafer is translationally moved along the second axis, thereby allowing the incident beam to cover the surface of the wafer. The beam scans the surface of the wafer by moving along a third axis perpendicular to the second axis. The inspection step comprises the emission of an incident beam of coherent light, the optical isolation preventing the reflected beam from attaining the emitting emitter, extension of the beam, also called an expansion, a scan transforming the static incident beam into an incident beam moving along a third axis perpendicular to the first and second axis by means of rotary polygonal mirror, and linearization of the movement of the beam relative to the focal plane. The linearization may be performed by means of an F-Theta lens.

In an embodiment, an inspection step comprises the simultaneous inspection of an upper surface and of a lower surface of the wafer with similar devices facing each other, the incident beams having different wavelengths. The difference in wavelengths may be greater than 2%. The difference in wavelengths may be greater than 10 nm.

In an embodiment, the inspection step comprises the shaping of the light scattered by the wafer, the detection of the scattered light by photomultipliers, and the processing of the detected light. The processing of the light may comprise the measurement of the amount of scattered light and matching the scattered light intensity with a given area of the wafer during two successive inspection steps at different angular positions of the wafer.

According to the selected mode, the inspection deals with the front face, the rear face or both faces of a substrate.

BRIEF DESCRIPTION OF THE DRAWINGS

The invention will be better understood upon reading the detailed description of a few embodiments taken as absolutely non-limiting examples and illustrated by the appended drawings, wherein.

DETAILED DESCRIPTION

At the end of their manufacturing, the semiconductor products, generally called semiconductor wafers, are inspected. Possible defects are sought, which generally appear as a shape heterogeneity at the surface of the wafer. This inspection should be conducted reliably and rapidly with a compact machine to the extent that an additional space occupied in a clean room is of a high cost.

More particularly, detecting defects with a sensitivity of the order of a few tens of nanometers, typically 50 nm on a polished silicon wafer or on another substrate, is required. The capability for detecting and characterizing these defects should not be very sensitive to the direction of the defect while being able to be carried out in less than 30 seconds on both faces of a wafer with a diameter of 300 mm. For this purpose, the applicants have developed the machine illustrated in FIG. 1. The machine comprises an upper emission route 1, a lower emission route 2, an upper reception route 3 and a lower reception route 4.

Figure 1:
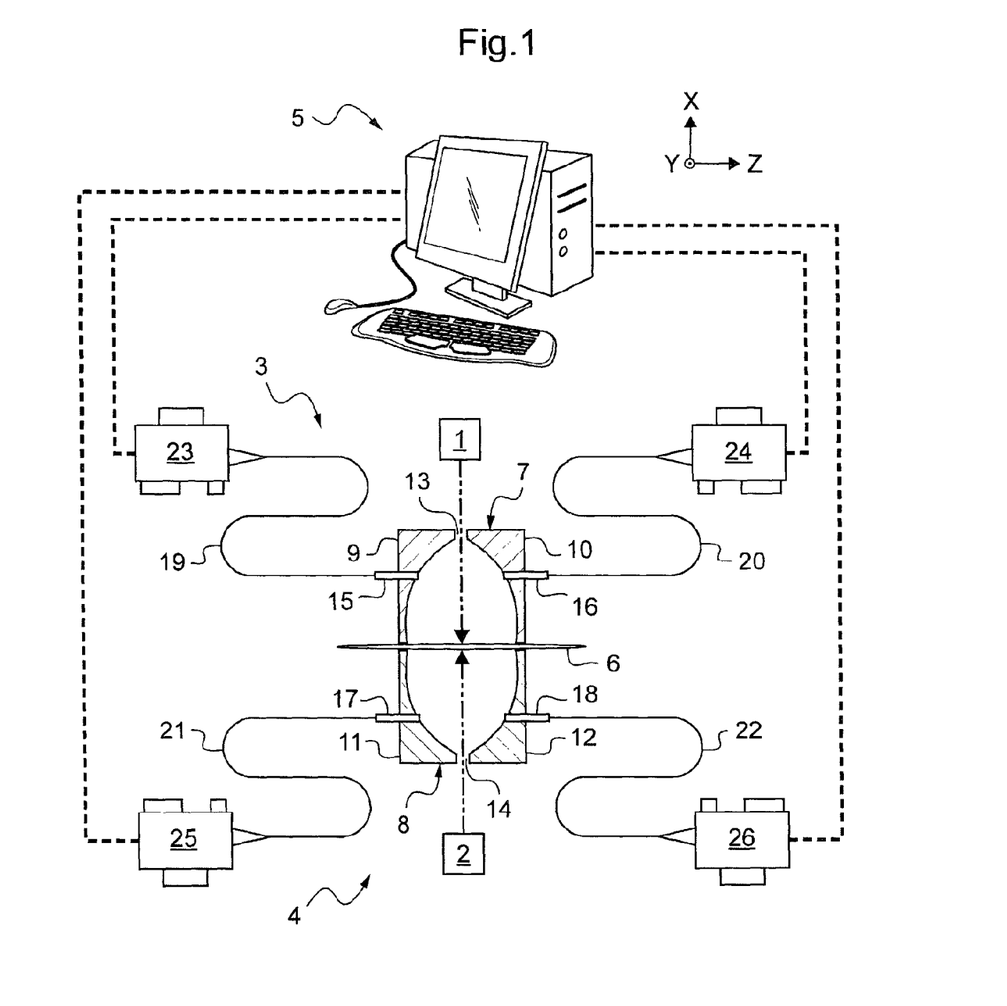
FIG. 1 is a schematic view of a device for inspecting semiconductor products.

The reception routes 3 and 4 are connected to an element 5 for analyzing the acquired data, for example, a computer provided with a software package for processing data from detectors. The emission routes 1 and 2 and the reception routes 3 and 4 have structures that are functionally symmetrical relative to the wafer 6 during inspection. The wafer 6 appears as a disc having a typical diameter of 100, 150, 200, 300 or 450 mm and a thickness which may range from a few hundred micrometers to a few millimeters. The emission routes 1 and 2 are also structurally symmetrical relative to the plane of the wafer 6.

Each reception route 3, 4 comprises an optical concentrator 7, 8. The optical concentrator 7, 8 appears as a cylindrical mirror (in the geometrical sense) with an axis Y while having a semi-elliptical sectional shape in the plane X-Z. The axis X is normal to the wafer 6. The length of the mirror along the Y axis is greater than the diameter of the wafer. The size of the concentrator 7, 8 along the axis Z may be less than the diameter of the wafer 6. This provides low bulkiness.

The concentrator 7, 8 comprises two symmetrical portions relative to the plane X-Y. The concentrator 7 of the reception route 3 comprises a first portion 9 and a second portion 10. The concentrator 8 of the reception route 4 comprises a first portion 11 and a second portion 12. The first and second portions of each concentrator 7, 8 are slightly disconnected in the vicinity of their plane of symmetry leaving a slit 13, 14 between the portions 9 and 10, 11 and 12. The incident beams emitted through the emission routes 1 and 2 respectively pass into the slits 13 and 14. The incident beam of the emission route 1, 2 is parallel to the axis X. The incident beam of the emission route 1, 2 is normal in the X-Z plane and quasi-normal in the X-Y plane to the corresponding surface of the wafer 6. The wafer 6 is positioned between the concentrators 7 and 8 at a small distance from their lower and respectively upper edges.

Each portion 9, 10, 11, 12 of the concentrators 7, 8 is provided with an elongated slit 15, 16, 17, 18 along the Y axis. The elongated slit 15, 16, 17, 18 is parallel to the slits 13 and 14. The elongated slit 15, 16, 17, 18 is positioned so that the light scattered by the wafer 6 illuminated with the incident beam from the emission routes 1, 2 is reflected by the surface of the mirror of the portions 9, 10, 11, 12 of the concentrator 7, 8 toward the slit 15, 16, 17, 18. Thus, in addition to the emission routes 1, 2, the concentrators 7, 8 are also symmetrical relative to the Y-Z plane. The first portion 9 is inscribed in an ellipse defined by a first focus located in the elongated slit 16 and a second focus located in the location common to the incident beam and to the upper surface of the wafer 6. The second portion 10 is inscribed in an ellipse defined by a first focus located in the elongated slit 15 and a second focus located in the location common to the incident beam and to the upper surface of the wafer 6. The first portion 11 is inscribed in an ellipse defined by a first focus located in the elongated slit 18 and a second focus located in the location common to the incident beam and to the lower surface of the wafer 6. The second portion 12 is inscribed in an ellipse defined by a first focus located in the elongated slit 17 and a second focus located in the location common to the incident beam and to the lower surface of the wafer 6.

The reception route 3, 4 comprises a web of optical fibers 19, 20, 21, 22 mounted in the slit 15, 16, 17, 18 for collecting the concentrated light in the slit and a detector 23, 24, 25, 26. The detector may be a photodiode or preferably a photomultiplier. The photomultiplier provides low noise level, a short response time, for example, of less than 2 ns and a sensitive area of significant size.

The analysis element 5 proceeds with thresholding. When the light intensity exceeds the threshold value defined by the user, the position (y, z) of the incident beam on the wafer 6 is recorded as well as the value of the maximum intensity IMAX of the light intensity peak. This information allows the construction of a localization map of the defects on the substrate as well as of their size.

Figure 2:
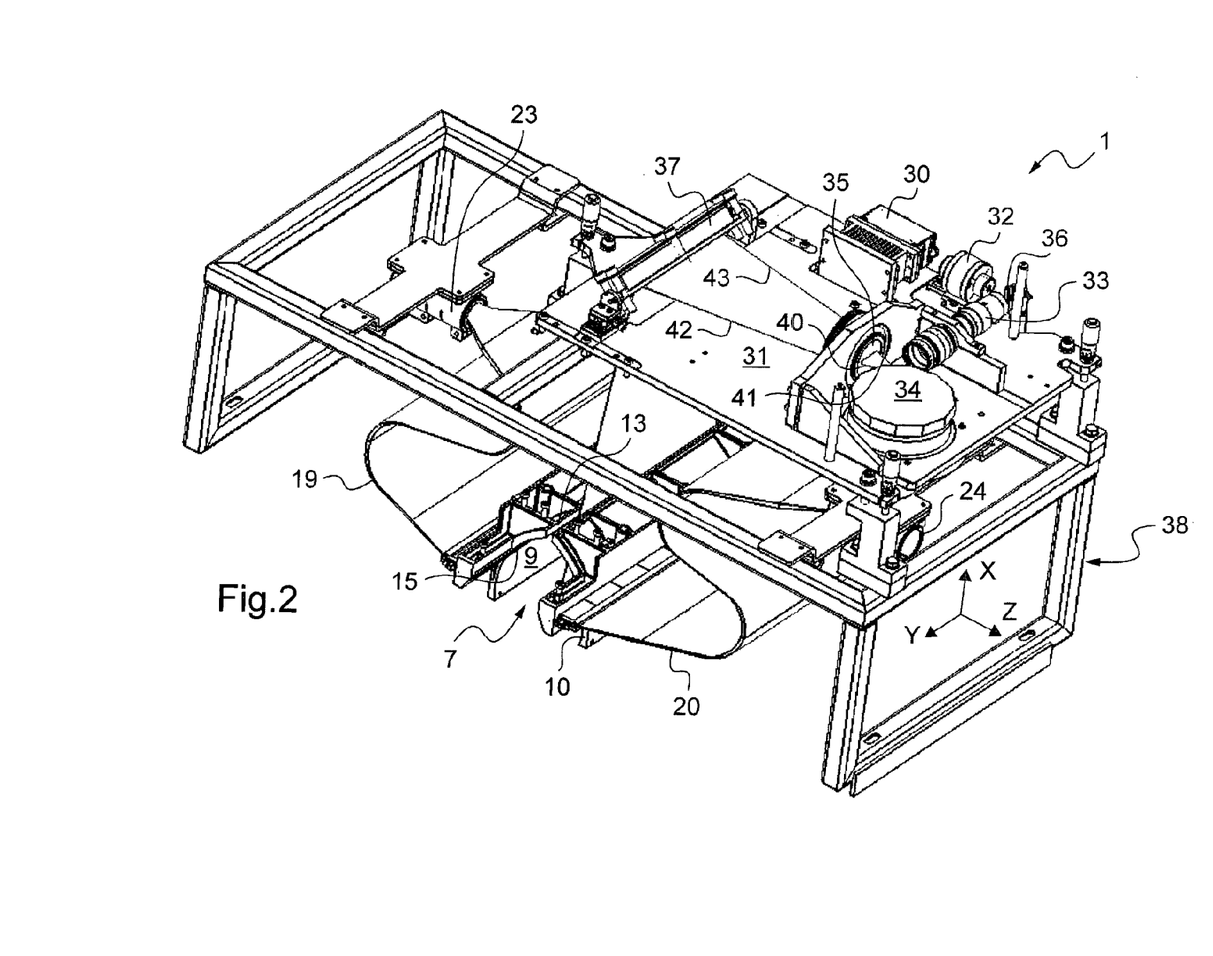
FIG. 2 is a perspective view of the emission route and of the reception route of the inspection device.

In FIG. 2, the emission route 1 and the reception route 3 have been illustrated. The webs of optical fibers 19 and 20 have at one end a length adapted to the one of the corresponding slit 15, 16 and at the end connected to the detector 23, 24, a grouped arrangement allowing application of a detector 23, 24 of compact structure. Moreover, the flexibility of the optical fibers gives the possibility of positioning the detector 23, 24 in a relatively free way relative to the slit 15, 16. Here, the detector 23, 24 is positioned clearly higher than the concentrator 7. In other words, the detectors 23, 24 are relatively distant from the location intended for the semiconductor wafer, which allows nearby space to be cleared.

Moreover, the detection of the positioning of a defect being independent of the optical fibers in that it is carried out according to the position of the incident beam and according to the position of the wafer along the Z axis, the information relating to the location from which stems such and such light signal is unnecessary, which allows simplification in the processing of the data.

The emission route 1 comprises a laser emitter 30 positioned on a plate 31, an optical isolator 32, a beam extender 33, a rotary polygonal mirror 34, an F-Theta lens 35. The plate 31 supports the laser emitter 30, the optical isolator 32, the beam extender 33, the rotary polygonal mirror 34 and the F-Theta lens 35. Further, provision is made for a deflecting mirror 36 and a deflecting rectangular mirror 37. The laser emitter 30 is capable of emitting a beam with a wavelength comprised between 330 nm and 670 nm at a power comprised between 1 and 200 mw. The laser emitter 30 is positioned for emitting a beam directed parallel to the Z axis. The optical isolator 32 prevents a beam reflected by the other optical elements or by the inspected surface from attaining the laser emitter 30. The laser emitter 30 may actually be destabilized by the reflected beam. The optical isolator 32 may be a polarization-dependent isolator. Any state of polarization not aligned with the optical isolator 32 is rejected or absorbed, therefore not transmitted to the laser emitter 30. The optical isolator 32 comprises a polarizer oriented with the polarization axis parallel to the polarization of the source to be isolated. The optical isolator 32, via the Faraday effect, causes rotation of the polarization of the incoming beam through a material with a strong Verdet constant, subject to a constant magnetic field from a permanent magnet. The beam of the return path also sees its polarization rotate in the same direction, the angle of rotation being added so that the total rotation is 90°. The beam of the return path for which the polarization is rotated by 90° is blocked by the polarizer in its propagation toward the source. The optical isolator 32 is positioned along the Z axis. The deflecting mirror 36 is positioned between the optical isolator 32 and the beam extender 33 and ensures deflection substantially at right angles.

The beam extender 33 is aligned parallel to the Y axis. The beam extender 33 may have a zoom factor of the order of 2 to 10. The beam extender 33 is of the Kepler type, i.e., with two lenses of positive focal length or Galilean, i.e., with one lens having a positive focal length and one lens having a negative focal length.

Figure 3:
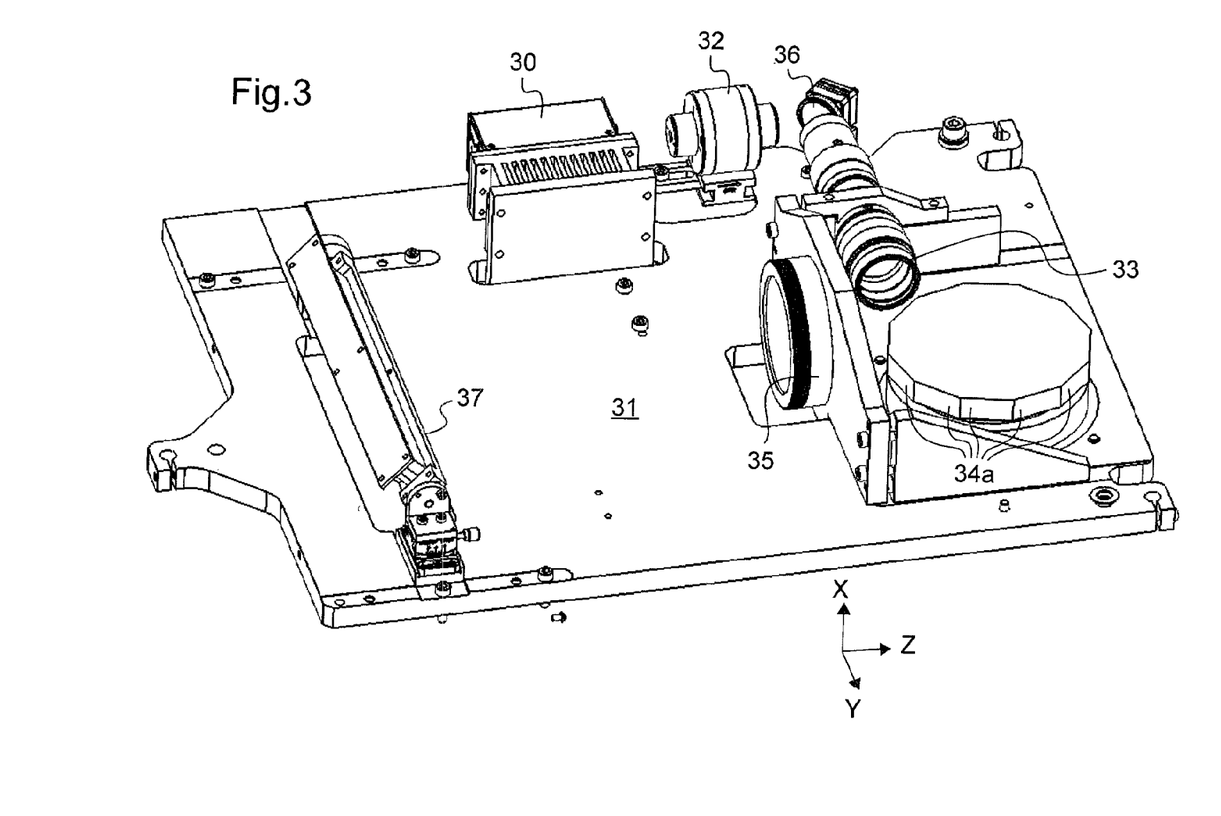
FIG. 3 is a detailed view of the emission route.
Figure 4:
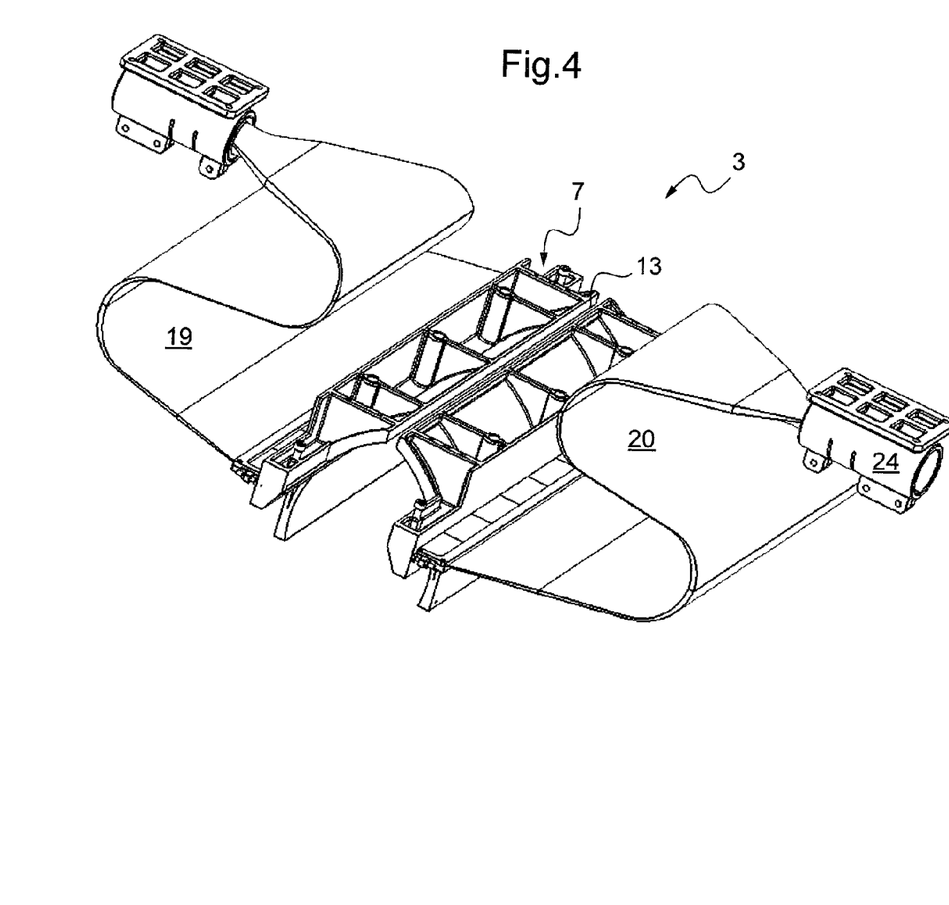
FIG. 4 is a detailed view of the reception route.
Figure 5:
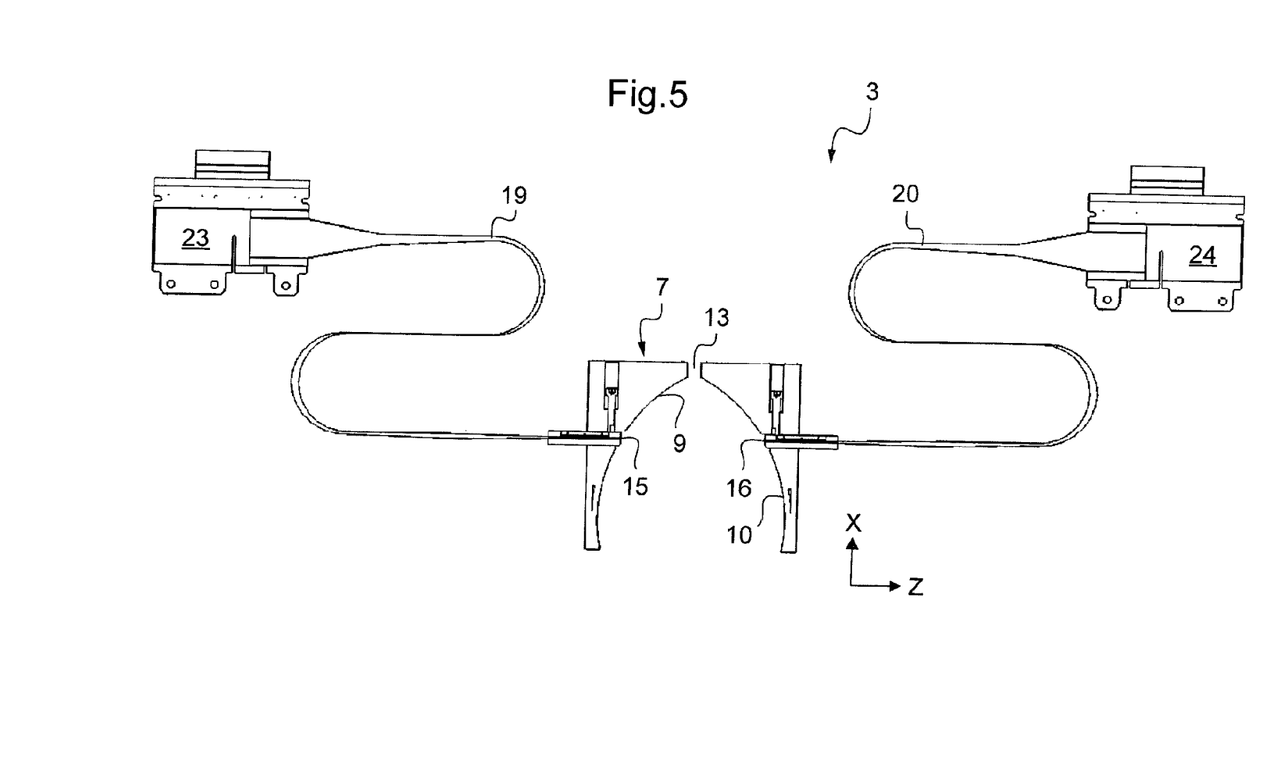
FIG. 5 is a sectional view of both reception routes.
Figure 6:
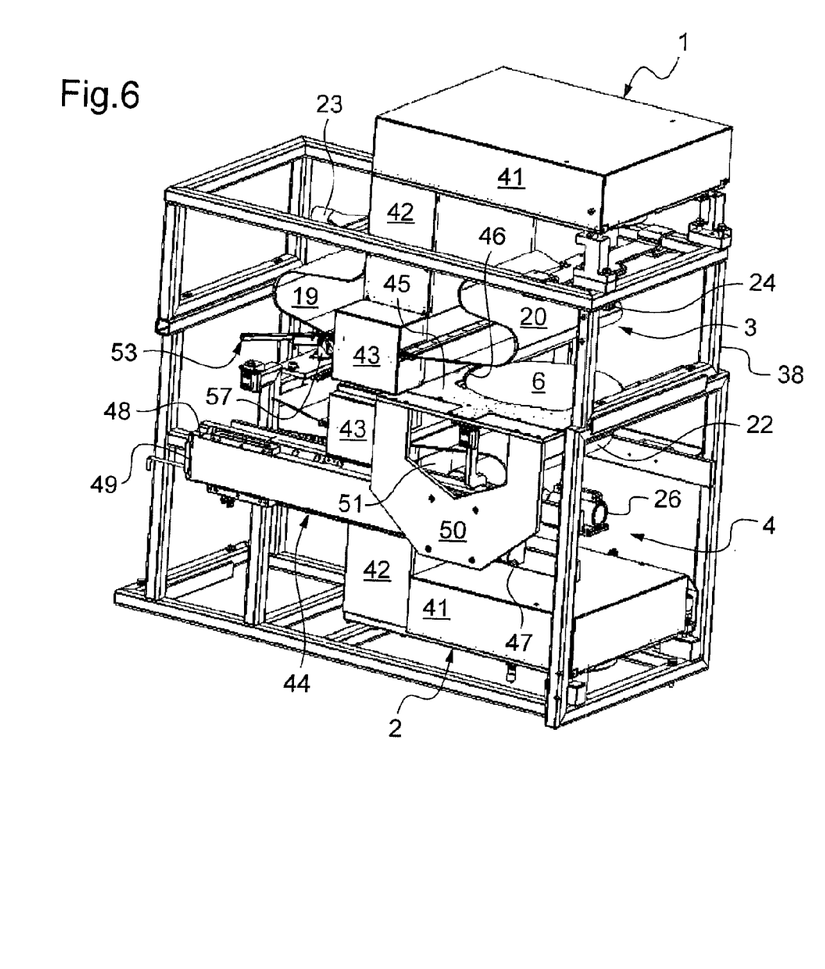
FIGS. 6 and 7 are two perspective views of the inspecting device, the upper inspection routes being covered and a mechanism for pivoting the semiconductor products being present.

The rotary mirror 34 is mounted with an axis of rotation parallel to the X axis downstream from the beam extender 33. The rotary mirror 34 comprises two substantially planar faces parallel to the Y-Z plane delimited by a polygonal contour forming regularly distributed facets 34a, as shown in FIG. 3. The facets 34a of the polygonal mirror 34 are mounted with central symmetry relative to an axis parallel to the X axis. The facets 34a are planar. The polygonal mirror 34 here comprises twelve facets. The polygonal mirror 34 is mounted relative to the beam extender 33 so that the beam from the beam extender 33 attains the facet 34a of the polygonal mirror 34 with an average angle of the order of 45°. The facets 34a of the polygonal mirror 34 reflect the emitted beam with the beam extender 33 toward the F-Theta lens 35, according to divergent limits.

In FIG. 2, the limits 40, 41 or extreme positions of the beam downstream from the polygonal mirror 34 have been illustrated. The scanning beam from the polygonal mirror 34 substantially moves in the Y-Z plane between extreme positions 40 and 41. The polygonal mirror 34 ensures deflection substantially at right angles to the expanded beam, from the beam extender 33. The angular position of the polygonal mirror 34 determines the position of the scanning beam. The polygonal mirror 34 is maintained at a stable speed of rotation giving the possibility of permanently knowing the angular position by simply acquiring a time-stamped signal emitted at each revolution of the mirror. The date of the signal and the elapsed time from the date by calculation gives the angular position of the mirror 34 and therefore the position of the incident beam.

The F-Theta lens 35 is positioned along the Z axis and receives the scanning beam at the exit of the polygonal mirror 34. The F-Theta lens 35 focuses in a plane the scanning beam received from the polygonal mirror 34. The F-Theta lens 35 linearizes the displacement of the beam relative to the focal plane. The F-Theta lens 35 allows the substrate to be scanned under normal or quasi-normal incidence while preserving the focal plane on the surface to be inspected, this by linearizing the displacement.

The linearized beam emitted by the F-Theta lens 35 is of divergent limits. The linearized beam is positioned in a plane parallel to the Y-Z plane. The linearized beam attains the rectangular deflecting mirror 37 and is displaced between limits 42 and 43. The rectangular deflecting mirror 37 sends back the linearized beam substantially at right angles in a plane parallel to the X, Y plane toward the slit 13 formed between the first portion 9 and the second portion 10 of the concentrator 7. The incident beam may then attain the wafer 6 visible in FIG. 1.

In the embodiment illustrated in FIG. 2, the whole of the elements of the emission route 1 are mounted on the plate 31 with a both modular and compact construction. The plate 31 may actually be disassembled for a maintenance or test operation, for example, on an optical test bench. The plate 31 and the detectors 23 and 24 rest on a frame 38.

Figure 7:
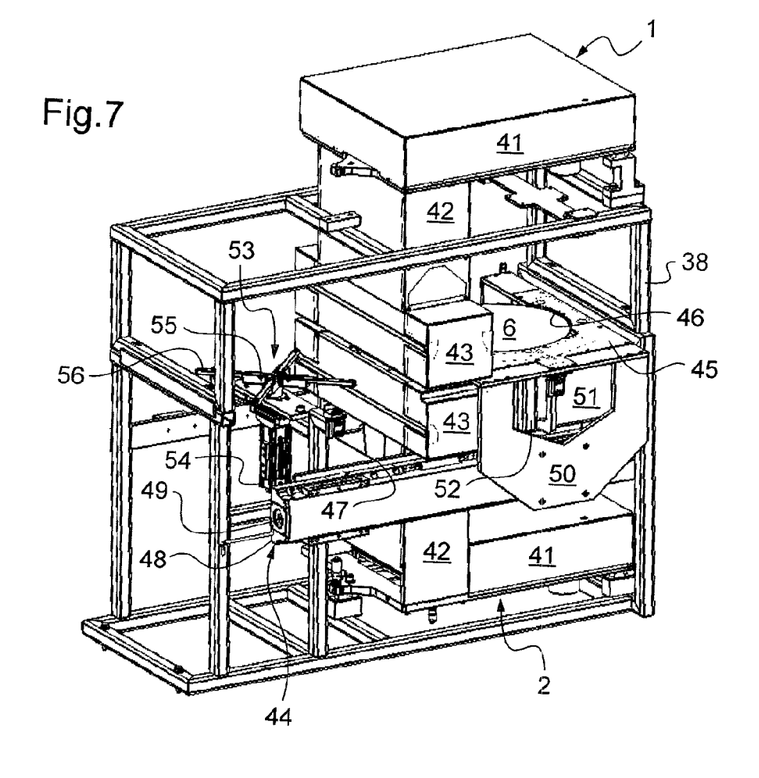
Figure 8:
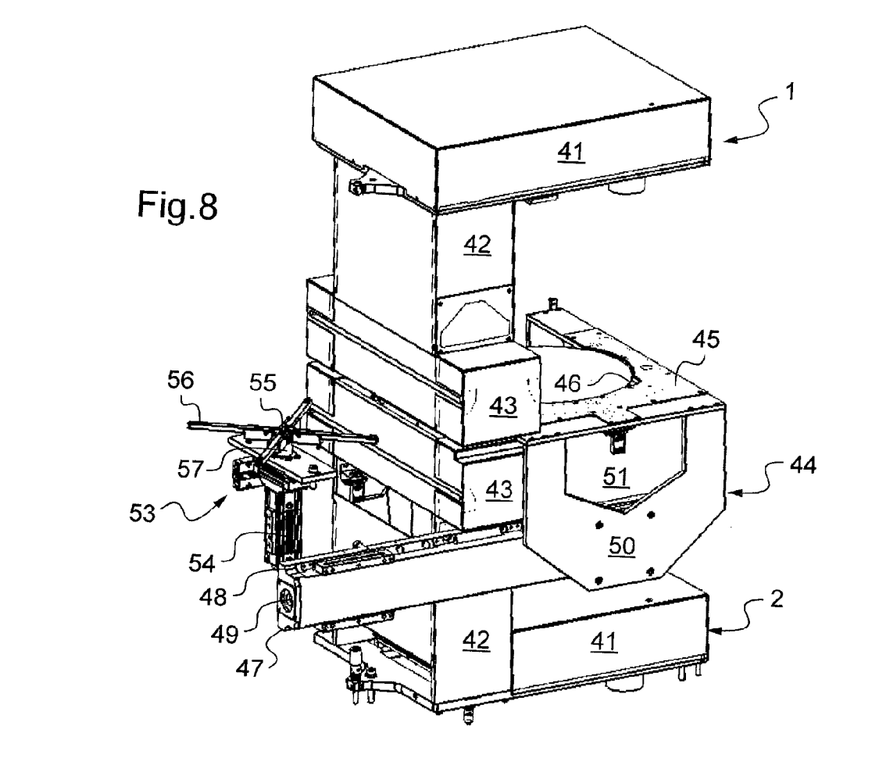
FIG. 8 is a perspective view of the mechanism for pivoting semiconductor products associated with the covered emission routes.
Figure 9:
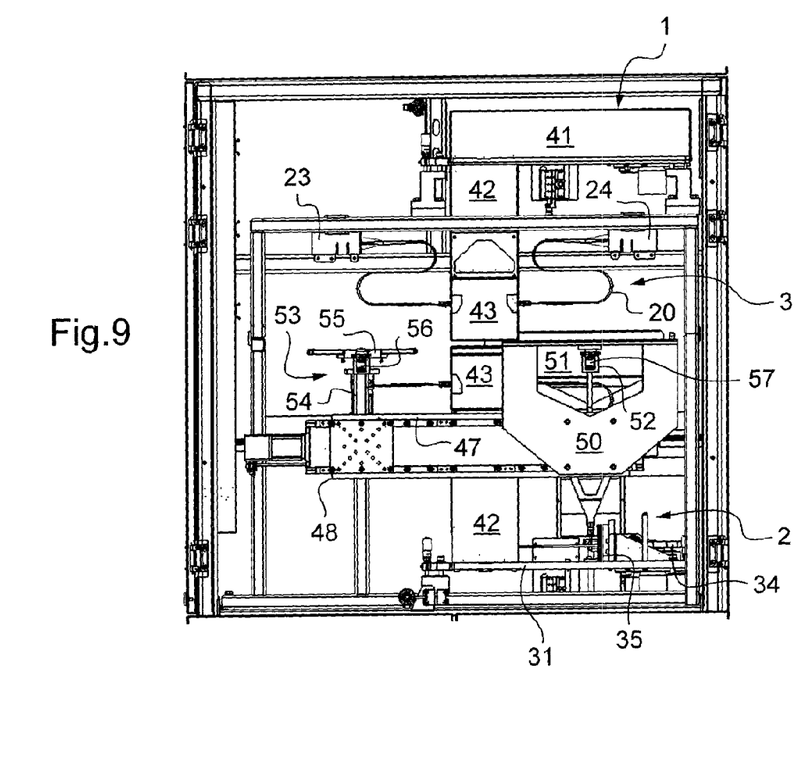
FIG. 9 is a front view of the inspection device.
Figure 10:
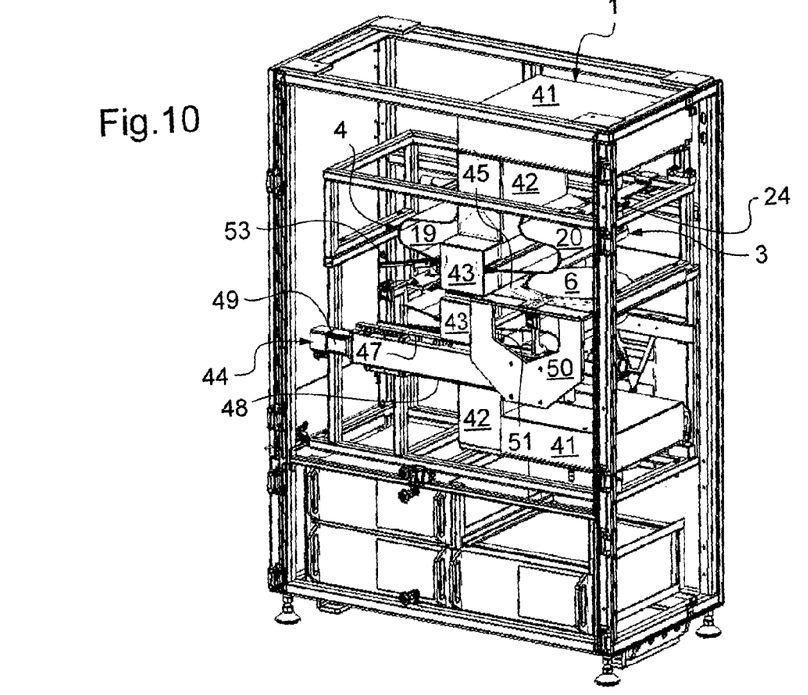
FIG. 10 is a perspective view of the inspection device.

In FIG. 7, the inspection device is shown with the emission routes 1, 2 and the reception routes 3, 4 protected by covers. A first cover 41 covers the plate 31. A second cover 42 surrounds the concentrator 7. A third cover 43 surrounds the beam between the rectangular deflecting mirror 37 and the concentrator 7. In FIG. 7, the webs of optical fibers and the detectors have been omitted. In FIG. 8, the frame 38 has been further omitted for better apprehension of the illustrated elements. In FIGS. 9 and 10, on the contrary, the frame 38, the webs of optical fibers 19 to 22 and the detectors 23 to 26 have been illustrated. Of course, caches are added at the end of the mounting of the inspection device in order to protect its elements and the operators next to the inspection device, and especially for trapping parasitic lights which would be scattered during its optical travel in order to limit the optical measurement noise.

The emission routes 1, 2 and the reception routes 3, 4 are stationary relative to the frame 38.

The inspection device comprises a mechanism 44 for moving the wafer 6, as shown in FIG. 8. The displacement mechanism 44 comprises a support 45 with a clamp provided with jaws 46 acting on the perimeter of the wafer 6. The jaws 46 may be in contact with an outer area of the lower and upper surfaces of the wafer 6. The outer area is of limited width, about 1 to 3 mm. The outer area is inactive from an electronic point of view. The displacement mechanism 44 comprises two slides 47, 48 of axis Z and a linear actuator 49 capable of displacing the clamp support 45 between a position for loading-unloading the wafer, a position for rotation of the wafer, and an inspection area. The linear actuator 49 is mounted on the slide 47. The slides 47, 48 are mounted on a bar of the frame 38. The slides 47, 48 are parallel. Between the slides 47, 48 and the clamp support 45, the displacement mechanism 44 comprises a lateral flange 50 on each side. Here, the flange 50 appears as a U-cut plate. The base of the flange 50 is attached to the slide 47, 48 and the top of the flange 50 is attached to the clamp support 45. At the center of the U, an aperture 51 is made in the flange 50 for facilitating maintenance. In FIG. 7, a mechanism for loading-unloading 52 the wafer 6 is visible through the aperture 51. The loading-unloading mechanism 52 may be part of the device or of another machine while interacting with the inspection device.

The loading-unloading position and the pivoting position are extreme positions. The inspection area begins in proximity to the loading-unloading position and ends at a distance from the pivoting position. In the loading-unloading position, the clamp support 45 is located on one side of the upper 7 and lower 8 concentrators along the Z axis. In the loading-unloading position, the jaws 46 are located between the plates 31 of the upper and lower emission routes 1, 2. In the pivoting position, the clamp support 45 is located on the other side of the upper 7 and lower 8 concentrators along the Z axis. The linear actuator 49 positions the wafer 6 translationally along the Z axis. The displacement mechanism 44 is supported by a lower portion of the frame 38.

On the side of the inspection device opposite to the loading-unloading mechanism 52, along the Z axis, a rotator 53 is mounted, capable of rotating the wafer 6 around the X axis. The rotator 53 is attached to the frame 38. The rotator 53 comprises an actuator 54 and a wafer support 55. The support 55 is mounted on a shaft of the actuator 54. The support 55 comprises a plurality of arms 56 in a star configuration, for example, a cross-bar with four arms. The arms 56 comprise an upper surface adapted for receiving a lower surface of the wafer 6. The upper surface of the arms 56 is positioned in the Y-Z plane. The rotator 53 is provided with a vertical translation actuator 57 with a small stroke, for example, of the order of a few millimeters, for lifting the wafer 6 and allowing its pivoting while avoiding contact with the jaws 46. The height of the upper surface of the arms 56 is adjusted so that the rotator 53 in translation upwards supports the wafer 6 over a small distance, the wafer 6 will then rest on the upper surface of the arms 56 while being free to rotate relative to the jaws 46. The rotator 53 then rotates the wafer 6 and then moves aside in translation downwards by means of the actuator 57. During displacement of the wafer 6 toward the pivoting position, the rotator 53 remains distant from the wafer 6 and from the displacement mechanism 44, the wafer 6 being free to move relative to the rotator 53 in the Y-Z plane.

Figure 11:
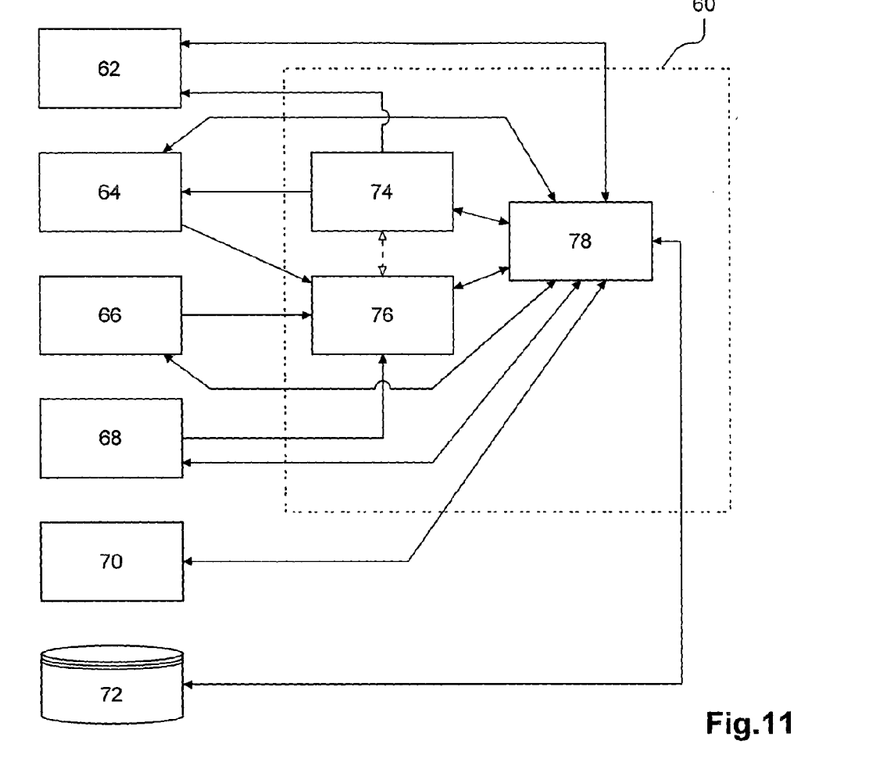
FIG. 11 is a view of the electrical diagram of the inspection device.

FIG. 11 illustrates a simplified view of the electronic diagram of the inspection device. As this may be seen in this figure, the inspection device comprises a control module 60, a source module 62, an illumination module 64, a reception module 66, a displacement module 68, a pivoting module 70, and a storage module 72.

The control module 60 comprises an illumination controller 74, a reception controller 76 and a central controller 78. The illumination controller 74 controls the source module 62 and the illumination module 64, and optionally exchanges synchronization data with the reception controller 76. The reception controller 76 controls the reception module 66 and receives data from the reception module 66 and from the displacement module 68. The central controller 78 controls the source module 62, an illumination module 64, the reception module 66, the displacement module 68, the pivoting module 70, the storage 72, the illumination controller 74 and the reception controller 76, and receives data in return from all these elements.

Figure 12:
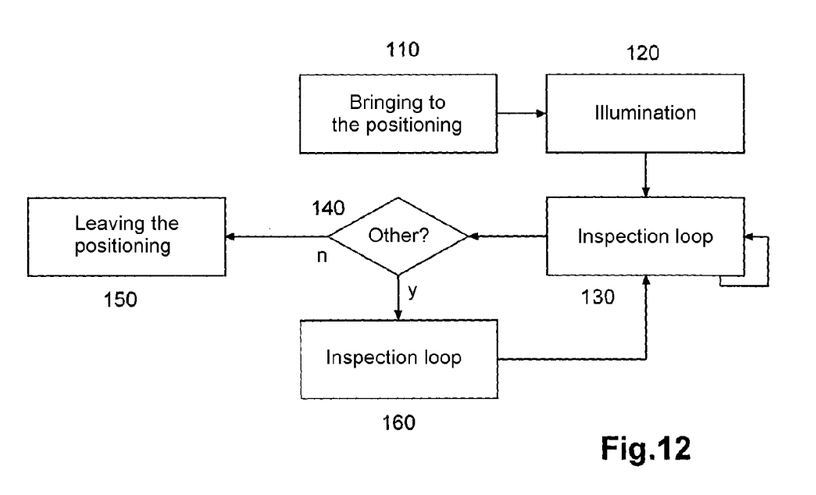
FIG. 12 is a flowchart of the steps of the inspection method.

FIG. 12 illustrates a general example of an inspection sequence. In an operation 110, the wafer 6 is brought and positioned. This includes the loading of the wafer 6 into the inspection device, by the loading-unloading mechanism 52, the taking into account of the wafer 6 by clamping the jaws 46 of the clamp support 45, and the displacement of the wafer 6 from the loading position to the inspection area, by translation of the displacement mechanism.

Next, with the rotary scanning mirror 34 rotating at a stable velocity, illumination is initiated in an operation 120, notably with the switching on of the laser emitter 30.

An acquisition loop is then executed in an operation 130. This loop comprises the beam traveling along a first line of the surface of the wafer 6 along the Y axis and the detection by the detector 23, 24 of the photons scattered by the surface of the wafer 6, reflected by the concentrator 7 and conveyed by the web of optical fibers 19, 20.

Next, the wafer 6 is moved within the inspection area by a distance or not less than the width of the beam along the Z axis, by translation of the displacement mechanism opposite to the loading position, and then the beam covers the next line and detection is repeated.

At the Nth iteration, the beam covers an Nth line of the surface of the wafer 6 along the Y axis and the detector 23, 24 detects photons scattered by the surface of the wafer 6, reflected by the concentrator 7 and conveyed by the web of optical fibers 19, 20. Next, the wafer 6 is displaced within the inspection area by a distance less than the width of the beam along the Z axis, by translation of the displacement mechanism 44 opposite to the loading position.

The loop is repeated until the last line of the surface of the wafer 6 has been covered by the beam, and an operation 140 then checks whether the wafer 6 has been scanned along all the desired directions. If this is the case, the wafer 6 is then taken out of the inspection device in an operation 150, which includes displacement of the wafer 6 from the inspection area to the unloading position, by translation of the displacement mechanism 44, the unclamping of the jaws 46 of the clamp support 45, and the unloading of the wafer 6 out of the inspection device, by the loading-unloading mechanism 52, as well as the switching off of the laser emitter 30.

When other inspection orientations are desired, the wafer 6 is pivoted in an operation 160. The operation 160 comprises the displacement of the wafer 6 from the inspection area to the pivoting position, by translation of the displacement mechanism 44, the unclamping of the jaws 46 of the clamp support 45 and the pressing of the wafer 6 onto the arms 56 of the rotator 53 by the upward movement of the rotator 53, the rotation of the wafer 6 by an angle comprised between 0 and 360°, excluding limits by the rotator 53, the downward movement of the rotator 53, the clamping of the jaws 46 of the clamp support 45. For this purpose, the actuator 57 causes vertical translation of the rotator 53 in order to lift the wafer 6 and allow its pivoting while avoiding contact with the stationary rotating jaws 46.

Next, the inspection sequence resumes with operation 130 along the new inspection direction with a direction for translating the displacement mechanism opposite to that of the loop of the operation 130 which has just been completed.

The example described here particularly provides the use of two inspection directions, at right angles from each other. Consequently, a single pivoting mechanism is required. If more than two inspection directions are desired, it is advantageous to provide mechanisms for pivoting the wafer at each end of the inspection device. As this has been seen above, once all the inspection directions have been used, the wafer is then taken out of the device in operation 150.

In the case of an inspection device with symmetrical upward/downward emission and reception routes, the steps for switching on the laser emitter 30, for having the beams cover the lines of the wafer 6 and for detection by the detectors 23 to 26, are substantially simultaneous. The wavelengths of the beams are different so that the light from a beam, either in the form scattered by the surface, or parasitic upon reflection or scattering by elements during the outbound or inbound optical path, may be discriminated, thereby allowing inspection of the surface opposite to the incident beam. For this purpose, the detectors 23 to 26 may comprise a frequency filter or be adjusted for detecting a specific wavelength with a sufficiently narrow bandpass. The notion of a line of the wafer is virtual: these are strips covered by the beam during the stepwise displacement of the wafer.

With each detection of a sufficient number of photons or of a sufficient light intensity, are associated the coordinates of the corresponding location of the surface of the wafer 6 determined by the position of the wafer 6, known by the position of the displacement 44 along the Z axis, and by the position of the beam along the Y axis known by the angular position of the rotary mirror 34.

The invention also relates to a device for inspecting semiconductor wafers, comprises a light source for emitting a plane incident beam toward a wafer, a member for shaping the light scattered by the wafer, a member for processing the shaped light, and a mechanism for rotating the wafer, comprising a multi-arm support configured for supporting the wafer and pivoting it by a selected angle. Alternatively, the multi-arm support may be configured in a star configuration.

The invention also relates to a device for inspecting semiconductor wafers, characterized in that it comprises two symmetrical portions for simultaneous inspection of opposite faces of a wafer, each portion comprising a light source for emitting a plane incident beam toward a wafer, a member for shaping the light scattered by the wafer, a filter receiving the shaped light, a member for processing the filtered light, the light sources of each portion being monochromatic with a wavelength shifted by at least 2%. This device may have a delta of 10 nm between the wavelengths used for each face.

The invention also relates to a device for inspecting semiconductor wafers, characterized in that it comprises a laser source for emitting an incident beam, a beam extender, a rotary polygonal mirror, and an F-Theta lens positioned downstream from the rotary polygonal mirror for linearizing the displacement of the beam relative to the focal plane.

This device may comprise a detecting mirror that may be rectangular, and/or a member for shaping the light scattered by the wafer, and/or a member for processing the shaped light, and/or an optical isolator, and/or may operate with a wide field.

The invention claimed is:

1. A device for inspecting semiconductor wafers, comprising, in this order:
    a light source for emitting an incident beam toward a wafer along a first axis;
    a concentrator that is symmetrical relative to a plane passing through the first axis and a second axis perpendicular to the first axis and provided with a cylindrical mirror having an elliptical cross-section along a plane perpendicular to the second axis, and having a generatrix parallel to the first axis;
    first and second parallel slits being made laterally in first and second portions of the concentrator at concentration points of the light scattered by the wafer and reflected by the second and first portions of the concentrator respectively; and
    one photomultiplier per slit.

2. The device of claim 1, wherein the length of the concentrator along the second axis is greater than the diameter of the wafer.

3. The device of claim 1, wherein a slit is made at the top of the concentrator in order to let through the incident beam, the slit being elongated along the second axis.

4. The device of claim 1, further comprising a member for holding the wafer through the edges of the wafer, comprising supporting fingers and at least one maintaining jaw.

5. The device of claim 1, further comprising a web of optical fibers positioned between each slit and the corresponding photomultiplier.

6. The device of claim 1, wherein the first axis is normal to the wafer.

7. The device of claim 1, further comprising a mechanism for translating the wafer relative to the incident beam, parallel to the first axis.

8. The device of claim 1, further comprising a mechanism for rotating the wafer relative to the incident beam, along an axis parallel with the second axis, comprising a multi-arm support configured for supporting the wafer and pivoting it by a selected angle.

9. The device of claim 1, wherein each portion of the concentrator has a first focus substantially positioned in the slit of the other portion and a second focus substantially positioned at an encounter point of the incident beam and of a surface of the wafer.

10. The device of claim 1, wherein the light source comprises, in this order, a laser emitter for emitting an incident beam, an optical isolator, a beam extender, a rotary polygonal mirror, and an F-Theta lens positioned downstream from the rotary polygonal mirror in order to linearize the displacement of the beam relative to the focal plane.

11. The device of claim 10, further comprising a first deflecting mirror positioned between the optical isolator and the beam extender, and a second deflecting mirror positioned between the F-Theta lens and the wafer.

12. A set of two devices for inspecting semiconductor wafers, positioned facing each other in order to simultaneously inspect both faces of a wafer with different incident beam wavelengths, wherein each device comprises, in this order:
    a light source for emitting an incident beam toward a wafer along a first axis;
    a concentrator that is symmetrical relative to a plane passing through the first axis and a second axis perpendicular to the first axis and provided with a cylindrical mirror having an elliptical cross-section along a plane perpendicular to the second axis, and having a generatrix parallel to the first axis;
    first and second parallel slits being made laterally in first and second portions of the concentrator at the concentration points of the light scattered by the wafer and reflected by the second and first portions of the concentrator respectively; and
    one photomultiplier per split.

* * * * *